(12) United States Patent
Patel et al.

(10) Patent No.: US 8,133,850 B2
(45) Date of Patent: Mar. 13, 2012

(54) DISPERSIONS COMPRISING HYDROXYPHENYLPYRUVATE DIOXYGENASE INHIBITORS

(75) Inventors: Smita Patel, Bremthal-Eppstein (DE); Romy Martin, Frankfurt (DE); Peter Baur, Schondorf (DE); Rainer Süssmann, Limburg (DE)

(73) Assignee: Bayer Cropscience AG, Monheim (DE)

( * ) Notice: Subject to any disclaimer, the term of this patent is extended or adjusted under 35 U.S.C. 154(b) by 220 days.

(21) Appl. No.: 12/631,072

(22) Filed: Dec. 4, 2009

(65) Prior Publication Data

US 2010/0144527 A1    Jun. 10, 2010

(30) Foreign Application Priority Data

Dec. 5, 2008   (EP) .................................... 08021143

(51) Int. Cl.
*A01N 43/82*   (2006.01)
*A01N 43/56*   (2006.01)
*A01N 43/08*   (2006.01)

(52) U.S. Cl. ........ 504/265; 504/280; 504/294; 504/248; 504/348

(58) Field of Classification Search .......... None
See application file for complete search history.

(56) References Cited

U.S. PATENT DOCUMENTS

| | | | |
|---|---|---|---|
| 2008/0004180 A1* | 1/2008 | Dollinger et al. ............. | 504/139 |
| 2009/0227563 A1* | 9/2009 | Fischer et al. ............ | 514/211.08 |

FOREIGN PATENT DOCUMENTS

| | | | |
|---|---|---|---|
| WO | 02/34047 | | 5/2002 |
| WO | 02/091831 | | 11/2002 |
| WO | 2006/079079 | | 7/2006 |
| WO | WO-2007068427 | * | 6/2007 |
| WO | 2008/135854 | | 11/2008 |
| WO | 2008/142391 | | 11/2008 |
| WO | WO-2008142391 | * | 11/2008 |

OTHER PUBLICATIONS

International Search Report of PCT/EP2009/008491 dated Feb. 2, 2011.
Ralph C. Kirkwood, "Use and Mode of Action of Adjuvants for Herbicides: A Review of some Current Work," Pestic. Sci., 1993, p. 93-102, vol. 38, UK.
European Search Report of EP08021143, dated May 11, 2009.

* cited by examiner

*Primary Examiner* — Alton Pryor
(74) *Attorney, Agent, or Firm* — Baker Donelson Bearman, Caldwell & Berkowitz, PC

(57) ABSTRACT

The present invention relates to dispersions comprising
  A) one or more herbicidal active substances from the group of the HPPD inhibitors,
  B) one or more oils,
  C) one or more surface-active substances,
  D) diammonium oxalate, diammonium hydrogen phosphate or ammonium dihydrogen phosphate,
  E) one or more rheological additives,
  F) optionally one or more agrochemical active substances other than A), such as herbicides, insecticides, fungicides, safeners or growth regulators,
  G) optionally formulation auxiliaries from the group consisting of antifoams, evaporation inhibitors, perfumes, colorants, antifreeze agents and preservatives.

The dispersions are suitable for use in the field of plant protection.

20 Claims, No Drawings

DISPERSIONS COMPRISING HYDROXYPHENYLPYRUVATE DIOXYGENASE INHIBITORS

CROSS REFERENCE TO RELATED APPLICATIONS

This application claims priority to European Application 08021143.6 filed Dec. 5, 2008.

BACKGROUND OF THE INVENTION

1. Field of the Invention

The present invention relates to the field of plant protection formulations. In particular, the invention relates to dispersions comprising herbicidal active substances which are known as hydroxyphenylpyruvate dioxygenase (HPPD) inhibitors.

2. Description of Related Art

Herbicidal active substances are conventionally not employed in their pure form. Depending on the field of application and the type of application, and on physical, chemical and biological parameters, the active substances are employed as active substance formulation as a mixture with customary adjuvants and additives. The combinations with further active substances for widening the spectrum of action and/or for protecting the crop plants (for example by safeners, antidotes) are also known.

In general, formulations of herbicidal active substances should have high chemical and physical stability, good application properties and user friendliness and a broad biological activity combined with high selectivity.

Hydroxyphenylpyruvate dioxygenase inhibitors are known as herbicides. Among these, benzobicyclon, isoxaflutole, mesotrione, pyrasulfotole, pyrazolynate, sulcotrione, tefuryltrione, tembotrione and topramezone are commercially available. Suspension concentrates or water-dispersible granules are already known as formulations of these active substances, see, for example, "The Pesticide Manual" 13th edition (2003), The British Crop Protection Council. EP 1 392 117 B1 discloses formulations of various hydroxyphenylpyruvate dioxygenase inhibitors in combination with certain fertilizers. WO 2008/135854-A2 discloses aqueous oil dispersions of 2-benzoyl-1,3-cyclohexanediones.

Depending on the intended use, the user demands formulations which are simple to handle and storage-stable. However, the formulations known from the prior art are not always satisfactory for these purposes.

SUMMARY OF THE INVENTION

It was an object of the present invention to provide formulations for active substances from the HPPD inhibitors series which do not have the abovementioned disadvantages.

This object is achieved by dispersions which, besides HPPD inhibitors, also comprise oil from the group of the vegetable and the mineral oils, surface-active substances, rheological additives and certain ammonium salts.

Accordingly, the present invention relates to dispersions comprising

A) one or more herbicidal active substances from the group of the HPPD inhibitors (component A),
B) one or more vegetable or mineral oils (component B),
C) one or more surface-active substances (component C),
D) a salt selected from the group consisting of diammonium oxalate, diammonium hydrogen phosphate and ammonium dihydrogen phosphate (component D), and
E) one or more rheological additives (component E).

Besides components A) to E), the dispersions according to the invention may also comprise further components F) and G), for example:

F) one or more agrochemical active substances other than A), such as herbicides, insecticides, fungicides, safeners or growth regulators, and
G) formulation auxiliaries such as antifoams, evaporation inhibitors, perfumes, colorants, antifreeze agents or preservatives.

DETAILED DESCRIPTION OF A PREFERRED EMBODIMENT

As a rule, the dispersions according to the invention are present as what are known as oil dispersions (OD) since the solid components, i.e. usually components A), D), E) and F), are in oil-dispersed form.

The dispersions according to the invention show outstanding storage stability and an outstanding herbicidal activity. The outstanding storage stability manifests itself in the solid components having only a very low tendency toward sedimentation and the active substances A) and F) decomposing only to a very small degree, even upon prolonged storage.

Usually, the dispersions according to the invention comprise

A) 1 to 25% of one or more herbicidal active substances from the group of the HPPD inhibitors,
B) 10 to 90% of one or more vegetable or mineral oils,
C) 0.5 to 40% of one or more surface-active substances,
D) 2 to 75% of diammonium oxalate, diammonium hydrogen phosphate or ammonium dihydrogen phosphate,
E) 0.1 to 4% of one or more rheological additives,
F) 0 to 20% of one or more agrochemical active substances other than A), such as herbicides, insecticides, fungicides, safeners or growth regulators,
G) 0 to 5% of formulation auxiliaries from the group consisting of antifoams, evaporation inhibitors, perfumes, colorants, antifreeze agents and preservatives.

Preferably, the dispersions according to the invention comprise

A) 2 to 15% of one or more herbicidal active substances from the group of the HPPD inhibitors,
B) 10 to 80% of one or more vegetable or mineral oils,
C) 0.5 to 30% of one or more surface-active substances,
D) 4 to 45% of diammonium oxalate, diammonium hydrogen phosphate or ammonium dihydrogen phosphate,
E) 0.1 to 4% of one or more rheological additives,
F) 1 to 10% of one or more agrochemical active substances other than A), such as herbicides, insecticides, fungicides, safeners or growth regulators,
G) 0 to 5% of formulation auxiliaries from the group consisting of antifoams, evaporation inhibitors, perfumes, colorants, antifreeze agents and preservatives.

All percentages are percent by weight.

Preferred herbicidal active substances from the group of the HPPD inhibitors are benzobicyclon, isoxaflutole, mesotrione, pyrasulfotole, pyrazolynate, sulcotrione, tefuryltrione, tembotrione, topramezone and 3-({2-[(2-methoxyethoxy)methyl]-6-(trifluoromethyl)pyridin-3-yl}carbonyl)bicyclo[3.2.1]octane-2,4-dione.

The abovementioned active substances are known to the skilled worker for example from "The Pesticide Manual" 14th Ed., British Crop Protection Council 2006, and the website "http://www.alanwood.net/pesticides/".

Some of the HPPD inhibitors have an acidic proton which may be removed by means of a base. The salts of the HPPD inhibitors which can thus be obtained are also suitable as component A) in the dispersions according to the invention. Examples of suitable bases are ammonia, the hydroxides, carbonates and hydrogen carbonates of zinc, alkali metals and alkaline earth metals such as sodium, potassium, calcium and magnesium, and organic bases of the formula $NR^1R^2R^3$ where $R^1$, $R^2$ and $R^3$ are in each case ($C_1$-$C_6$)-alkyl, ($C_2$-$C_6$)-alkenyl or ($C_2$-$C_6$)-alkynyl, and $R^2$ and $R^3$ can additionally also be hydrogen. The potassium, sodium and ammonium salts are preferred.

Suitable oils of group B) are vegetable oils and mineral oils. The term vegetable oils means, for the purposes of the present invention, oils from oil-producing plant species such as soybean oil, rapeseed oil, corn oil, sunflower oil, cottonseed oil, linseed oil, coconut oil, palm oil, safflower oil or castor oil, in particular rapeseed oil, and their transesterification products, for example alkyl esters, such as rapeseed oil methyl esters.

The vegetable oils are preferably esters of $C_{10}$-$C_{22}$-, preferably $C_{12}$-$C_{20}$-fatty acids. The $C_{10}$-$C_{22}$-fatty acid esters are, for example, esters of unsaturated or saturated $C_{10}$-$C_{22}$-fatty acids, in particular those with an even number of carbon atoms, for example erucic acid, lauric acid, palmitic acid and in particular $C_{18}$-fatty acids such as stearic acid, oleic acid, linoleic acid or linolenic acid.

Examples of $C_{10}$-$C_{22}$-fatty acid esters are esters which are obtained by reacting glycerol or glycol with the $C_{10}$-$C_{22}$-fatty acids, as they are present for example in oils from oil-producing plant species, or $C_1$-$C_{20}$-alkyl-$C_{10}$-$C_{22}$-fatty acid esters as they can be obtained for example by transesterification of the abovementioned glycerol or glycol $C_{10}$-$C_{22}$-fatty acid esters with $C_1$-$C_{20}$-alcohols (for example methanol, ethanol, propanol or butanol). The transesterification can be carried out by known methods as they are described, for example, in the Römpp Chemie Lexikon, 9th edition, volume 2, page 1343, Thieme Verlag Stuttgart.

Preferred as $C_1$-$C_{20}$-alkyl-$C_{10}$-$C_{22}$-fatty acid esters are methyl esters, ethyl esters, propyl esters, butyl esters, 2-ethylhexyl esters and dodecyl esters. Preferred as glycol and glycerol $C_{10}$-$C_{22}$-fatty acid esters are the individual or mixed glycol esters and glycerol esters of $C_{10}$-$C_{22}$-fatty acids, in particular those fatty acids with an even number of carbon atoms, for example erucic acid, lauric acid, palmitic acid and in particular $C_{18}$-fatty acids such as stearic acid, oleic acid, linoleic acid or linolenic acid.

In the dispersions according to the invention, the vegetable oils can be present for example in the form of commercially available oil-containing formulation additives, in particular those based on rapeseed oil, such as Hasten® (Victorian Chemical Company, Australia, hereinbelow referred to as Hasten, main component: rapeseed oil ethyl ester), Actirob®B (Novance, France, hereinbelow referred to as ActirobB, main component: rapeseed oil methyl ester), Rako-Binol® (Bayer AG, Germany, hereinbelow referred to as Rako-Binol, main component: rapeseed oil), Renol® (Stefes, Germany, hereinbelow referred to as Renol, vegetable oil constituent: rapeseed oil methyl ester) or Stefes Mero® (Stefes, Germany, hereinbelow referred to as Mero, main constituent: rapeseed oil methyl ester).

Examples of mineral oils are aliphatic or aromatic hydrocarbons such as toluene, xylenes and naphthalene derivatives, in particular 1-methylnaphthalene, 2-methyl-naphthalene, $C_6$-$C_{16}$-aromatic mixtures such as, for example, the Solvesso® series (ESSO) with the types Solvesso® 100 (b.p. 162-177° C.), Solvesso® 150 (b.p. 187-207° C.) and Solvesso® 200 (b.p. 219-282° C.) and mixtures of hydrocarbons comprising ($C_6$-$C_{20}$)-aliphatics which may be linear or cyclic, such as the products of the Shellsol® series, types T and K, or BP-n paraffins.

Suitable surface-active substances C) are, for example, surfactants based on nonaromatics, for example on the basis of heterocycles, olefins, aliphatics or cycloaliphatics, for example surface-active pyridine, pyrimidine, triazine, pyrrole, pyrrolidine, furan, thiophene, benzoxazole, benzthiazole and triazole compounds which are substituted by one or more alkyl groups and which have subsequently been derivatized, for example alkoxylated, sulfated, sulfonated or phosphated, and/or surfactants based on aromatics, for example benzenes or phenols which are substituted by one or more alkyl groups and which have subsequently been derivatized, for example alkoxylated, sulfated, sulfonated or phosphated. In general, the surface-active substances C) are soluble in the oil phase and suitable for emulsifying the latter together with the active substances dissolved therein upon dilution with water (to give the spray mixture). The dispersions according to the invention may comprise for example nonaromatic or aromatic surfactants or mixtures of nonaromatic and aromatic surfactants.

Examples of surface-active substances C) are listed hereinbelow, with EO representing ethylene oxide units, PO propylene oxide units and BO butylene oxide units:

C1) $C_{10}$-$C_{24}$-Alcohols, which can be alkoxylated, e.g., with 1-60 alkylene oxide units, preferably 1-60 EO and/or 1-30 PO and/or 1-15 BO, in any sequence. The terminal hydroxyl groups of these compounds may be end-capped by an alkyl, cycloalkyl or acyl radical with 1-24 carbon atoms. Examples of such compounds are: Genapol® C, L, O, T, UD, UDD, X products from Clariant, Plurafac® and Lutensol® A, AT, ON, TO products from BASF, Marlipal® 24 and O13 products from Condea, Dehypon® products from Henkel, Ethylan® products from Akzo-Nobel such as Ethylan CD 120.

C2) Anionic derivatives of the products described under C1) in the form of ether carboxylates, sulfonates, sulfates and phosphates and the inorganic (e.g., alkali metal and alkaline earth metal) and organic (e.g., amine- or alkanolamine-based) salts thereof, such as Genapol® LRO, Sandopan® products, Hostaphat/Hordaphos® products from Clariant. Copolymers consisting of EO, PO and/or BO units, such as, for example, block copolymers, such as the Pluronic® products from BASF and the Synperonic® products from Uniquema, with a molecular weight of 400 to $10^8$. Alkylene oxide adducts of $C_1$-$C_9$-alcohols, such as Atlox® 5000 from Uniquema or Hoe® S3510 from Clariant.

C3) Fatty acid and triglyceride alkoxylates, such as the Serdox® NOG products from Condea or alkoxylated vegetable oils, such as soybean oil, rapeseed oil, corn oil, sunflower oil, cottonseed oil, linseed oil, coconut oil, palm oil, safflower oil, walnut oil, peanut oil, olive oil or castor oil, in particular rapeseed oil, the term "vegetable oils" also being understood as meaning the transesterification products thereof, e.g. alkyl esters, such as rapeseed oil methyl ester or rapeseed oil ethyl ester, for example the Emulsogen® products from Clariant, salts of aliphatic, cycloaliphatic and olefinic carboxylic acids and polycarboxylic acids, and α-sulfofatty acid esters, as available from Henkel.

C4) Fatty acid amide alkoxylates such as the Comperlan® products from Henkel or the Amam® products from Rhodia. Alkylene oxide adducts of alkyne diols such as the Surfynol® products from Air Products. Sugar derivatives such as amino and amido sugars from Clariant, glucitols from Clariant, alkylpolyglycosides in the form of APG® products from Henkel or such as sorbitan esters in the form of Span® or Tween® products from Uniquema or cyclodextrin esters or ethers from Wacker.

C5) Surface-active cellulose and algin, pectin and guar derivatives such as the Tylose® products from Clariant, the Manutex® products from Kelco and guar derivatives from Cesalpina. Alkylene oxide adducts based on polyols such as the Polyglykol® products from Clariant. Surface-active polyglycerides and the derivatives thereof from Clariant.

C6) Alkanesulfonates, paraffinsulfonates and olefinsulfonates such as Netzer IS®, Hoe® S1728, Hostapur® OS, Hostapur® SAS from Clariant.

C7) Alkylene oxide adducts from fatty amines, quaternary ammonium compounds with 8 to 22 carbon atoms ($C_8$-$C_{22}$) such as, e.g., the Genamin® C, L, O, T products from Clariant.

C8) Surface-active, zwitterionic compounds such as taurides, betaines and sulfobetaines in the form of Tegotain® products from Goldschmidt, Hostapon® T and Arkopon® T products from Clariant.

C9) Surface-active compounds based on silicones or silanes such as the Tegopren® products from Goldschmidt and the SE® products from Wacker, and also the Bevaloid®, Rhodorsil® and Silcolapse® products from Rhodia (Dow Corning, Reliance, GE, Bayer).

C10) Per- or polyfluorinated surface-active compounds such as Fluowet® products from Clariant, the Bayowet® products from Bayer, the Zonyl® products from DuPont and products of this type from Daikin and Asahi Glass.

C11) Surface-active sulfonamides, e.g. from Bayer.

C12) Surface-active polyacrylate and polymethacrylate derivatives, such as the Sokalan® products from BASF.

C13) Surface-active polyamides, such as modified gelatin or derivatized polyaspartic acid from Bayer and their derivatives.

C14) Surfactant polyvinyl compounds such as modified polyvinyl pyrrolidone such as the Luviskol® products from BASF and the Agrimer® products from ISP or derivatized polyvinyl acetates such as the Mowilith® products from Clariant or the polyvinyl butyrates, such as the Lutonal® products from BASF, the Vinnapas® and the Pioloform® products from Wacker, or modified polyvinyl alcohols, such as the Mowiol® products from Clariant.

C15) Surface-active polymers based on maleic anhydride and/or reaction products of maleic anhydride, and also copolymers comprising maleic anhydride and/or reaction products of maleic anhydride, such as the Agrimer® VEMA products from ISP.

C16) Surface-active derivatives of montan, polyethylene and polypropylene waxes such as the Hoechst® wax or Licowet® products from Clariant.

C17) Surface-active phosphonates and phosphinates, such as Fluowet® PL from Clariant.

C18) Poly- or perhalogenated surfactants, such as, for example, Emulsogen® 1557 from Clariant.

C19) Phenols, which may be alkoxylated, for example phenyl ($C_1$-$C_4$)alkyl ethers or (poly)alkoxylated phenols [=phenol (poly)alkylene glycol ethers], for example with 1 to 50 alkyleneoxy units in the (poly)alkyleneoxy part, the alkylene part preferably exhibiting 1 to 4 carbon atoms each time, preferably phenol reacted with 3 to 10 mol of alkylene oxide, (poly)alkylphenols or (poly)alkylphenol alkoxylates [=polyalkylphenol(poly)alkylene glycol ethers], for example with 1 to 12 carbon atoms per alkyl radical and 1 to 150 alkyleneoxy units in the polyalkyleneoxy part, preferably tri(n-butyl)phenol or triisobutylphenol reacted with 1 to 50 mol of ethylene oxide, polyarylphenols or polyarylphenol alkoxylates [=polyarylphenol(poly)alkylene glycol ethers], for example tristyrylphenol polyalkylene glycol ethers with 1 to 150 alkyleneoxy units in the polyalkyleneoxy part, preferably tristyrylphenol reacted with 1 to 50 mol of ethylene oxide.

C20) Compounds which are formally the reaction products of the molecules described under C19) with sulfuric acid or phosphoric acid and the salts thereof neutralized with suitable bases, for example the acidic phosphoric ester of triethoxylated phenol, the acidic phosphoric ester of a nonylphenol reacted with 9 mol of ethylene oxide and the phosphoric ester, neutralized with triethanolamine, of the reaction product of 20 mol of ethylene oxide and 1 mol of tristyrylphenol.

C21) Benzenesulfonates, such as alkyl- or arylbenzenesulfonates, e.g. (poly)alkyl- and (poly)arylbenzenesulfonates which are acidic and neutralized with suitable bases, for example having 1 to 12 carbon atoms per alkyl radical or having up to 3 styrene units in the polyaryl radical, preferably (linear) dodecylbenzene-sulfonic acid and the oil-soluble salts thereof, such as, for example, the calcium salt or the isopropylammonium salt of dodecylbenzenesulfonic acid.

Ethyleneoxy, propyleneoxy and butyleneoxy units, in particular ethyleneoxy units, are preferred for the alkyleneoxy units.

Examples of surface-active substances from the group of the nonaromatic-based surfactants are the surfactants of the abovementioned groups C1) to C18), preferably the groups C1), C2), C6) and C7). Examples of surface-active substances from the group of the aromatic-based surfactants are the surfactants of the abovementioned groups C19) to C21) preferably phenol reacted with 4 to 10 mol of ethylene oxide, available commercially, for example, in the form of the Agrisol® products (Akcros), triisobutylphenol reacted with 4 to 50 mol of ethylene oxide, available commercially, for example, in the form of the Sapogenat® T products (Clariant), nonylphenol reacted with 4 to 50 mol of ethylene oxide, available commercially, for example, in the form of the Arkopal® products (Clariant), tristyrylphenol reacted with 4 to 150 mol of ethylene oxide, for example from the Soprophor® series, such as Soprophor® FL, Soprophor® 3D33, Soprophor® BSU, Soprophor® 4D-384, Soprophor® CY/8 (Rhodia), and acidic (linear) dodecylbenzenesulfonate, available commercially, for example, in the form of the Marlon® products (Hüls).

Preferred surface-active substances C) are e.g. alkoxylated $C_{10}$-$C_{24}$-alcohols (C1) and the anionic derivatives thereof (C2) such as sulfates, sulfonates and phosphates, alkoxylated vegetable oils (C3), alkoxylated phenols (C19) and their reaction products with sulfuric acid or phosphoric acid (C20), and alkylbenzene-sulfonates (C21).

It is preferred to employ ammonium dihydrogen phosphate as component D).

To control the sedimentation behavior of the dispersed components A), D) and, if appropriate, F), the dispersions comprise, as component E), rheological additives which are also known as thickeners. Those which are suitable in this context are synthetic or natural mineral products and/or in particular those organic rheological additives which are suitable for nonaqueous formulations.

Substances which are suitable from the class of the mineral rheological additives are pure silicas, for example of the ®Sipernat, ®Wessalon types or surface-treated silicates such as ®Aerosil from Degussa, or mixed oxides, for example magnesium aluminum silicates such as attapulgite (®Attagel 40, Attagel 50 from Engelhard) or magnesium layered silicates such as bentonites or hectorites. An example of an especially suitable substance is ®Aerosil R202.

Further suitable organic additives for influencing the rheological properties of the formulation are thickeners and/or thixotropic agents from the group of specific polyamides such as ®Thixa SR, ®Mixatrol SR 100 or ®Mixatrol TSR and polyesters such as ®Thixatrol 289; all products from Rheox. Products which are based on castor oil such as ®Thixicia E, ®Thixain R, ®Thixatrol ST or ®Thixatrol GST, also from Rheox, have proved to be particularly effective for preventing the sedimentation of the HPPD inhibitor.

Agrochemical active substances F) which are suitable for the inventive dispersions, other than component A) and which may optionally be present are, in particular the known herbicides mentioned hereinbelow, as they are described, for example, in Weed Research 26, 441-445 (1986), or "The Pesticide Manual", 14th edition, The British Crop Protection Council, 2006, and the literature cited therein, for example in mixed formulations or as partners in tank mixers. The compounds are referred to either by their "common name" according to the International Organization for Standardization (ISO) or by their chemical name, if appropriate together with a customary code number, and always comprise all use forms such as acids, salts, esters and isomers such as stereoisomers and optical isomers: acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy] acetic acid and its methyl ester; alachlor; alloxydim; ametryn; amitrole; AMS, i.e. ammonium sulfamate; anilofos; asulam; atrazin; azafenidine (DPX-R6447), aziprotryn; barbane; BAS 516 H, i.e. 5-fluoro-2-phenyl-4H-3,1-benzoxazin-4-one; benazolin; benfluralin; benfuresate; bensulide; bentazone; benzofluor; benzoylprop-ethyl; benzthiazuron; bialaphos; bifenox; bispyribac-sodium (KIH-2023), bromacil; bromobutide; bromofenoxim; bromoxynil, in particular bromoxynil octanoate and bromoxynil heptanoate; butachlor; butamifos; butenachlor; buthidazole; butralin; butroxydim (ICI-0500), butylate; cafenstrole (CH-900); carbetamide; cafentrazone; CDAA, i.e. 2-chloro-N,N-di-2-propenylacetamide; CDEC, i.e. 2-chloroallyl diethyldithiocarbamate; chlomethoxyfen; chloramben; cloransulam-methyl (XDE-565), chlorazifop-butyl, chlorbromuron; chlorbufam; chlorfenac; chlorflurenol-methyl; chloridazon; chlornitrofen; chlorotoluron; chloroxuron; chlorpropham; chlorthal-dimethyl; chlorthiamid; cinidon-ethyl, cinmethylin; clethodim; clodinafop and its ester derivatives (for example clodinafop-propargyl); clomazone; clomeprop; cloproxydim; clopyralid; cumyluron (JC 940); cyanazine; cycloate; cycloxydim; cycluron; cyhalofop and its ester derivatives (for example the butyl ester, DEH-112); cyperquat; cyprazine; cyprazole; 2,4-D; 2,4-DB; dalapon; desmedipham; desmetryn; di-allate; dicamba; dichlobenil; dichlorprop; diclofop and its esters such as diclofop-methyl; diclosulam (XDE-564), diethatyl; difenoxuron; difenzoquat; diflufenican; diflufenzopyr-sodium (SAN-835H), dimefuron; dimethachlor; dimethametryn; dimethenamid (SAN-582H); dimidazone, methyl 5-(4,6-dimethylpyrimidin-2-yl-carbamoylsulfamoyl)-1-(2-pyridyl)-pyrazole-4-carboxylate (NC-330); triaziflam (IDH-1105), cinosulfon; dimethipin, dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-1H-pyrazole-4-carboxamide; endothal; indanofan (MK-243), EPTC; esprocarb; ethalfluralin; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl] phenyl]ethanesulfonamide; ethoxyfen and its esters (for example the ethyl ester, HN-252); etobenzanid (HW 52); 3-(4-ethoxy-6-ethyl-1,3,5-triazin-2-yl)-1-(2,3-dihydro-1,1-dioxo-2-methylbenzo[b]thiophen-7-sulfonyl)urea (EP-A 079 683); 3-(4-ethyl-6-methoxy-1,3,5-triazin-2-yl)-1-(2,3-dihydro-1,1-dioxo-2-methylbenzo[b]-thiophen-7-sulfonyl) urea (EP-A 079 683); fenoprop; clomazone, fenoxaprop and fenoxaprop-P and their esters, for example fenoxaprop-P-ethyl and fenoxaprop-ethyl; butroxydimfenuron; flamprop-methyl; flufenacet (BAY-FOE-5043), fluazifop and fluazifop-P and their esters, for example fluazifop-butyl and fluazifop-P-butyl, florasulam (DE-570); fluchloralin; flumetsulam; fluometuron; flumiclorac and its esters (for example the pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fluthiacet-methyl (KIH-9201), fomesafen; fosamine; furyloxyfen; glufosinate; glyphosate; halosafen; halosulfuron and its esters (for example the methyl ester, NC-319); haloxyfop and its esters; haloxyfop-P (=R-haloxyfop) and its esters; hexazinone; imazamethabenz-methyl; imazamox (AC-299263), imazapyr; imazaquin and salts such as the ammonium salt; imazapic; imazethapyr; imazosulfuron; ioxynil; isocarbamid; isopropalin; isoproturon; isouron; isoxaben; isoxapyrifop; karbutilate; actofen; lenacil; linuron; MCPA; MCPB; mecoprop; mefenacet; mefluidid; metamitron; metazachlor; methabenzthiazuron; metam; methazole; methoxyphenone; methyldymron; metobenzuron, mesosulfuron-methyl, mesosulfuron-methyl (WO 95/10507); metobromuron; metolachlor; S-metolachlor, metosulam (XRD 511); metoxuron; metribuzin; maleic hydrazide; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; foramsulfuron (WO 95/01344); naproanilide; napropamide; naptalam; NC 310, i.e. 4-(2,4-dichlorobenzoyl)-1-methyl-5-benzyloxypyrazole; neburon; nipyraclophen; nitralin; nitrofen; nitrofluorfen; norflurazon; orbencarb; oryzalin; oxadiargyl (RP-020630); oxadiazon; oxaziclomefone (MY-100), oxyfluorfen; paraquat; pebulate; pendimethalin; pentoxazone (KPP-314), perfluidone; phenisopham; phenmedipham; picloram; pinoxaden; piperophos; pyributicarb; pirifenop-butyl; pretilachlor; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prynachlor; pyraflufen-ethyl (ET-751), chloridazon; pyrazoxyfen; pyribenzoxim, pyridate; pyriminobac-methyl (KIH-6127), pyrithiobac (KIH-2031); pyroxofop and its esters (for example the propargyl ester); quinclorac; quinmerac; quizalofop, quizalofop and quizalofop-P and their ester derivatives, for example quizalofop-ethyl; quizalofop-P-tefuryl and -ethyl; S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; flazasulfuron (FMC-97285, F-6285); sulfazuron; glyphosate-trimesium (ICI-A0224); TCA; tebutam (GCP-5544); tebuthiuron; tepraloxydim (BAS-620H), terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thiencarbazone-methyl; thidiazimin (SN-124085); thiobencarb; tiocarbazil; tralkoxydim; tri-allate; triazofenamide; triclopyr;

tridiphane; trietazine; trifluralin; trimeturon; vernolate; WL 110547, i.e. 5-phenoxy-1-[3-(trifluoromethyl)phenyl]-1H-tetrazole; UBH-509; D-489; LS 82-556; KPP-300; KPP-421, MT-146, NC-324; butenachlor (KH-218); DPX-N8189; haloxyfop-etotyl (DOWCO-535); DK-8910; flumioxazin (V-53482); PP-600; MBH-001, amicarbazone, aminopyralid, beflubutamid, benzobicyclon, benzofenap, benzfendizone, butafenacil, chlorfenprop, cloprop, daimuron, dichlorprop-P, dimepipeate, dimethenamid-P, fentrazamide, flamprop-M, fluazolate, indanofan, isoxachlortole, MCPA-thioethyl, mecoprop-P, mesotrione, metamifop, penoxsulam, pethoxamid, picolinafen, profluazol, profoxydim, pyraclonil, pyrazolynate, pyridafol, pyriftalid and thidiazuron. The following are preferred: atrazine, bromoxynil, foramsulfuron, metolachlor, S-metolachlor and terbuthylazine. Bromoxynil may be employed in each case in the form of its potassium salt, heptanoate or octanoate.

Further agrochemical active substances F) other than component A) which are suitable for the dispersions according to the invention and which are optionally present are, in particular, the safeners mentioned hereinbelow, as they are described in, for example, Weed Research 26, 441-445 (1986) or "The Pesticide Manual", 14th edition, The British Crop Protection Council, 2006, and in the literature cited therein, for example in mixed formulations or as partners in tank mixers: mefenpyr-diethyl, isoxadifen-ethyl, cloquintocet-mexyl, cyprosulfamid, fenchlorazol-ethyl, dichlormid, benoxacor. Isoxadifen-ethyl is preferred.

The following may additionally be present in the dispersions according to the invention as conventionally used adjuvants and additives G): for example wetters, antidrift agents, adhesives, penetrants, preservatives, antifreeze agents, antioxidants, fillers, carriers, colorants, perfumes, antifoams, evaporation inhibitors, pH modulators, viscosity modulators and agents which have a positive effect on stability, in particular the stability to hydrolysis. These are known in principle and are described, for example, in standard works: McCutcheon's "Detergents and Emulsifiers Annual", MC Publ. Corp., Ridgewood, N.J.; Sisley and Wood, "Encyclopedia of Surface active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976; Winnacker-Küchler, "Chemische Technologie" [Chemical technology], volume 7, C. Hauser-Verlag, Munich, 4th edition 1986.

Suitable antifreeze agents are those from the group of the ureas, diols and polyols, such as ethylene glycol and propylene glycol. Suitable antifoams are those which are silicone-based. Suitable structure-imparting agents are those from the group of the xanthans. Suitable preservatives, colorants and perfumes are known to the skilled worker.

The dispersions according to the invention can be prepared by customary processes which are already known, for example by mixing the various components with the aid of stirrers, shakers, mills or (static) mixers. Usually, the solid components are employed in finely-ground form.

The dispersions according to the invention show significantly improved application behavior, and manifests itself in markedly reduced sieve residues or clogging of sieves or nozzles. The application rate of the dispersions according to the invention per hectare generally varies between 0.5 and 5 liters, preferably between 1.0 and 4.0 liters.

For use, the dispersions according to the invention may be diluted in a customary manner, for example to give suspensions, emulsions or suspoemulsions, for example by means of water. It may be advantageous to add, to the spray mixtures obtained, further agrochemical active substances (for example partners for tank mixers in the form of suitable formulations) and/or adjuvants and additives conventionally used for application, for example autoemulsifying oils such as vegetable oils or liquid paraffin and/or further fertilizers. The present invention therefore also relates to the herbicidal compositions prepared in this manner.

Usually, the ratio of dispersion according to the invention to water amounts to from 1:500 to 1:50. The spray mixture per ha is usually 50 to 500 liters, preferably 75 to 350 liters of water. In some cases, the concentrations may also fall short of, or exceed, the limits detailed herein. The dispersions are also suitable for aerial application. To this end, dispersions according to the invention are applied either in undiluted form or diluted with water or with organic solvents. In this context, the volume of additional carrier liquid will, as a rule, vary from 0.5 to 50 liters per hectare. The present invention therefore also relates to such herbicidal compositions based on the dispersions according to the invention.

The dispersions or herbicidal compositions according to the invention have an outstanding herbicidal activity against a broad spectrum of economically important monocotyledonous and dicotyledonous harmful plants. The activity also extends to weeds which sprout from rhizomes, root stocks or other perennial organs and which are difficult to control. In this context, the compositions may be applied for example before sowing, pre-emergence or post-emergence. Specifically, some representatives of the monocotyledonous and dicotyledonous weed flora which can be controlled by the herbicidal compositions according to the invention may be mentioned by way of example, without the mention being intended as a restriction to certain species: among the monocotyledonous weed species, good activity is effected on, for example, *Apera spica venti*, *Avena* spp., *Alopecurus* spp., *Brachiaria* spp., *Digitaria* spp., *Lolium* spp., *Echinochloa* spp., *Panicum* spp., *Phalaris* spp., *Poa* spp., *Setaria* spp. and *Bromus* spp. such as *Bromus catharticus*, *Bromus secalinus*, *Bromus erectus*, *Bromus tectorum* and *Bromus japonicus* and *Cyperus* species from among the annuals, and, among the perennial species, *Agropyron*, *Cynodon*, *Imperata* and *Sorghum* and also perennial *Cyperus* species. Among the dicotyledonous weed species, the spectrum of action extends to species such as, for example, *Abutilon* spp., *Amaranthus* spp., *Chenopodium* spp., *Chrysanthemum* spp., *Galium* spp. such as *Galium aparine*, *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp. among the annuals and *Convolvulus*, *Cirsium*, *Rumex* and *Artemisia* among the perennial weeds.

The compositions according to the invention also effect outstanding control of harmful plants which are found under the specific culture conditions in rice, such as, for example, *Echinochloa*, *Sagittaria*, *Alisma*, *Eleocharis*, *Scirpus* and *Cyperus*.

If the herbicidal compositions according to the invention are applied to the soil surface before germination, either the emergence of the weed seedlings is prevented completely, or the weeds grow until they have reached the cotyledon stage, but then their growth stops and they eventually die completely after three to four weeks have elapsed.

When the herbicidal compositions according to the invention are applied post-emergence to the green parts of the plant, their growth also stops drastically very soon after the treatment, and the weed plants remain at the growth stage present at the time of application or die fully after a certain time has elapsed, so that, in this manner, competition by weeds, which is harmful to the crop plants, is eliminated at a very early point in time and in a sustained manner.

The herbicidal compositions according to the invention are distinguished by a herbicidal activity with a rapid onset and long persistence. The rainfastness of the active substances in the combinations according to the invention is, as a rule, advantageous. A particular advantage is that the dosage rates of herbicidal compounds which are effective and which are used in the herbicidal compositions can be adjusted to such a low level that their soil action is as low as possible. This not only makes possible their use in sensitive crops for the first time, but also contaminations of the ground water are virtually avoided. The combination according to the invention of active substances makes possible a considerable reduction of the required application rate of the active substances.

The abovementioned properties and advantages are useful in practical weed control in order to keep agricultural crops free from undesired competing plants, thereby safeguarding and/or increasing the yields in terms of quality and quantity. These novel compositions markedly outperform the technical standard with regard to the above-described properties.

Although the herbicidal compositions have an outstanding herbicidal activity against monocotyledonous and dicotyledonous weeds, crop plants of economically important crops, for example dicotyledonous crops such as soybean, cotton, oilseed rape, sugar beet, or Gramineae crops such as wheat, barley, rye, oats, sorghum/millet, rice or maize are only damaged to a negligible extent, or not at all. This is why the herbicidal compositions according to the invention are highly suitable for the selective control of undesired vegetation in stands of agriculturally useful plants or in stands of ornamentals.

Moreover, the herbicidal compositions according to the invention have outstanding growth-regulatory properties in crop plants. They engage in the plants' metabolism in a regulatory fashion and can therefore be employed for the targeted control of plant constituents and for facilitating harvesting such as, for example, by triggering desiccation and stunted growth. Moreover, they are also suitable for generally controlling and inhibiting undesired vegetative growth without killing the plants in the process. Inhibiting the vegetative growth plays an important role in many monocotyledonous and dicotyledonous crops since lodging can thereby be reduced or prevented completely.

Owing to their herbicidal and plant-growth-regulatory properties, the herbicidal compositions according to the invention can also be used for controlling harmful plants in crops of genetically modified plants which are known or yet to be developed. As a rule, the transgenic plants are distinguished by special advantageous properties, for example by resistances to certain pesticides, mainly certain herbicides, resistances to plant diseases or pathogens of plant diseases, such as certain insects or microorganisms such as fungi, bacteria or viruses. Other special properties relate for example to the harvested material with regard to quantity, quality, storability, composition and specific constituents. Thus, transgenic plants are known which have an increased starch content or a modified starch quality, or those which have different fatty acid composition of the harvested material.

Preferred is the use of the herbicidal compositions according to the invention in economically important transgenic crops of useful plants and ornamentals, for example Gramineae crops such as wheat, barley, rye, oats, sorghum/millet, rice and maize, or else crops of sugar beet, cotton, soybean, oilseed rape, potato, tomato, pea and other vegetables. Preferably, the compositions according to the invention can be employed as herbicides in crops of useful plants which are resistant, or have been made resistant by means of genetic engineering, to the phytotoxic effects of the herbicides.

When using the herbicidal compositions according to the invention in transgenic crops, activities which are specific to the application in the respective transgenic crop can frequently be observed, in addition to the activities which can be observed in other crops, for example a modified or specifically extended weed spectrum which can be controlled, modified application rates which may be employed for application, preferably good combining ability with the herbicides to which the transgenic crop is resistant, and an influence on the growth and yield of the transgenic crop plants.

The present invention furthermore also relates to a method of controlling undesirable vegetation, preferably in crops of plants such as cereals (for example wheat, barley, rye, oats, rice, maize, sorghum/millet), sugar beet, sugar cane, oilseed rape, cotton and soybean, especially preferably in monocotyledonous crops such as cereals, for example wheat, barley, rye, oats, crosses of these such as triticale, rice, maize and sorghum/millet, where one or more herbicidal compositions according to the invention are applied to the harmful plants, plant parts, plant seeds or the area in which the plants grow, for example the area under cultivation.

The plant crops may also have been genetically modified or may have been obtained by mutation selection and are preferably tolerant to acetolactate synthase (ALS) inhibitors.

USE EXAMPLES

The terms used in the examples hereinbelow denote:
Solvesso 200 ND=mixture of aromatics (b.p. 219-282° C.)
Witconate P-1860=calcium sulfonate
Emulsogen EL 400=ethoxylated castor oil with 40 ethylene oxide units
Genapol X-060=nonionic surfactant based on ethoxylated isotridecanol-polyglycol ether
Aerosil R202=hydrophobic silica Use Example Preparation of a Dispersion According to the Invention

TABLE 1

| Component | Amount |
|---|---|
| A) Tembotrione | 4.31 g |
| B) Rapeseed oil methyl ester | 43.82 g |
| B) Solvesso 200 ND | 15.00 g |
| C) Atplus 309 F-LM | 9.00 g |
| C) Witconate P-1860 | 3.00 g |
| C) Emusolgen EL 400 | 3.00 g |
| C) Genapol X-060 | 1.00 g |
| D) Ammonium dihydrogen phosphate | 14.71 g |
| E) Aerosil R202 | 4.00 g |
| F) Isoxadifen-ethyl | 2.16 g |

Component C) is initially introduced in dissolved form into component B). Then, the finely-ground components A), E), D) and F) are added little by little with stirring, and stirring is continued until a homogeneous dispersion has formed.

The resulting dispersion according to the invention is storage-stable over a prolonged period. Even upon prolonged storage, the solid constituents show only a very low tendency to form a sediment. Even upon prolonged storage, the active substance A) and G) show only a very low degree of decomposition. The dispersion according to the invention can be diluted with water to give a homogeneous suspoemulsion. It has outstanding activity against harmful plants while simultaneously being very well tolerated in crops of useful plants.

The storage stability of the formulation according to the invention, which is increased in comparison to a prior-art formulation comprising ammonium hydrogen sulfate, manifests itself for example in the form of a lesser degree of decomposition of the active substance of group A) upon storage at different temperatures. To this end, a first experiment involved preparing the abovementioned formulation according to the invention and, for comparison purposes, a similar formulation comprising ammonium hydrogen sulfate instead of ammonium dihydrogen phosphate in each case in accordance with the above-described method and storing the products for 8 weeks at 40° C. In a second experiment, the degree of decomposition of the active substance of group A) was determined after storage for 8 weeks at a temperature of 40° C. The results in table 3 show that the formulation according to the invention shows a lower composition of the active substance of group A) than the formulation comprising ammonium hydrogen sulfate with the same ingredients.

TABLE 2

| Component | According to the invention Amount | Comparative formulation Amount |
| --- | --- | --- |
| A) Tembotrione | 4.31 g | 4.31 g |
| B) Rapeseed oil methyl ester | 43.82 g | 43.82 g |
| B) Solvesso 200 ND | 15.00 g | 15.00 g |
| C) Atplus 309 F-LM | 9.00 g | 9.00 g |
| C) Witconate P-1860 | 3.00 g | 3.00 g |
| C) Emusolgen EL 400 | 3.00 g | 3.00 g |
| C) Genapol X-060 | 1.00 g | 1.00 g |
| D) Ammonium dihydrogen phosphate | 14.71 g | 0 g |
| D) Ammonium hydrogen sulfate | 0 g | 14.71 g |
| E) Aerosil R202 | 4.00 g | 4.00 g |
| F) Isoxadifen-ethyl | 2.16 g | 2.16 g |

TABLE 3

| Formulation | Decomposition of the active substance tembotrione after storage | |
| --- | --- | --- |
| | 8 weeks at 21° C. | 8 weeks at 40° C. |
| According to the invention | 0% | 2.6% |
| Comparison | 4.6% | 7.9% |

We claim:

1. A dispersion comprising
   A) 1 to 25% of one or more herbicidal active substances from the group of the hydroxyphenylpyruvate dioxygenase(HPPD) inhibitors,
   B) 10 to 90% of one or more vegetable or mineral oils,
   C) 0.5 to 40% of one or more surface-active substances,
   D) 2 to 75% of diammonium oxalate, diammonium hydrogen phosphate or ammonium dihydrogen phosphate,
   E) 0.1 to 4% of one or more rheological additives,
   F) 0 to 20% of one or more agrochemical active substances other than A),
   G) 0 to 5% of the formulation auxiliaries selected from the group consisting of antifoams, evaporation inhibitors, perfumes, colorants, antifreeze agents and preservatives.

2. The dispersion as claimed in claim 1, comprising
   A) 2 to 15% of one or more herbicidal active substances from the group of the HPPD inhibitors,
   B) 10 to 80% of one or more vegetable or mineral oils,
   C) 5 to 30% of one or more surface-active substances,
   D) 4 to 45% of diammonium oxalate, diammonium hydrogen phosphate or ammonium dihydrogen phosphate,
   E) 0.1 to 4% of one or more rheological additives,
   F) 1 to 10% of one or more agrochemical active substances other than A), selected from the group consisting of herbicides, insecticides, fungicides, safeners or growth regulators,
   G) 0 to 5% of formulation auxiliaries selected from the group consisting of antifoams, evaporation inhibitors, perfumes, colorants, antifreeze agents and preservatives.

3. The dispersion as claimed in claim 1, wherein the HPPD inhibitors are selected from the group consisting of benzobicyclon, isoxaflutole, mesotrione, pyrasulfotole, pyrazolynate, sulcotrione, tefuryltrione, tembotrione, topramezone and 3-({2-[(2-methoxyethoxy)methyl]-6-(trifluoromethyl)pyridin-3-yl}carbonyl)bicyclo [3.2.1] octane-2,4-dione.

4. The dispersion as claimed in claim 3, comprising, as herbicidal active substance, tembotrione.

5. The dispersion as claimed in claim 1, comprising, as component D), ammonium dihydrogen phosphate.

6. The dispersion as claimed in claim 1, comprising, wherein F) is present and comprises isoxadifen-ethyl.

7. A liquid herbicidal composition, obtainable by diluting the dispersion as claimed in claim 1.

8. A method of controlling undesired vegetation, comprising applying an effective amount of the dispersion as claimed in claim 1 to plants, parts of the plants, plant seed or the area in which plants grow.

9. The method of controlling undesired vegetation according to claim 8, wherein said effective amount of a dispersion is from 0.5 and 5.0 liters per hectare.

10. The method of controlling undesired vegetation according to claim 9, wherein said effective amount of a dispersion is from 1.0 and 4.0 liters per hectare.

11. The method of controlling undesired vegetation according to claim 8, wherein the ratio of the dispersion to water is from about 1:500 to 1:50.

12. The method of controlling undesired vegetation according to claim 8, wherein application is an aerial application.

13. The dispersion according to claim 1, wherein said one or more herbicidal active substances is tembotrione and said one or more vegetable or mineral oils is a rapeseed oil methyl ester.

14. The dispersion according to claim 1, wherein said one or more vegetable or mineral oils is selected from the group consisting of soybean oil, rapeseed oil, corn oil, sunflower oil, cottonseed oil, linseed oil, coconut oil, palm oil, safflower oil, castor oil, rapeseed oil transesterification products, and rapeseed oil methyl esters.

15. The dispersion according to claim 1, wherein said one or more vegetable or mineral oils is selected from the group consisting of a rapeseed oil methyl ester and C6-C16 aromatic mixtures having boiling point ranging from 219 degree C. to 282 degree C.

16. The dispersion according to claim 1, wherein said one or more surface-active substances is a surfactant.

17. The dispersion according to claim 1, wherein said one or more surface-active substances is selected from the group consisting of calcium sulfonate, ethoxylated castor oil with 40 ethylene oxide units and nonionic surfactant based on ethoxylated isotridecanol-polyglycol ether.

18. The dispersion according to claim 1, wherein said component F) is present in an amount of from 1% to 10%.

19. The dispersion according to claim 1, wherein said component G) is present and selected from the group consisting of consisting of antifoams, evaporation inhibitors, perfumes, colorants, antifreeze agents and preservatives.

20. The dispersion according to claim 1 comprising
A) 1 to 25% of tembotrione;
B) 10 to 90% of rapeseed oil methyl ester;
C) 0.5 to 40% of one or more surfactants;
D) 2 to 75% of ammonium dihydrogen phosphate;
E) 0.1 to 4% of one or more rheological additives;
F) 0 to 20% of one or more agrochemical active substances other than A), and
G) 0 to 5% of the formulation auxiliaries selected from the group consisting of antifoams, evaporation inhibitors, perfumes, colorants, antifreeze agents and preservatives.

* * * * *